United States Patent
Beck et al.

(10) Patent No.: US 6,837,637 B1
(45) Date of Patent: Jan. 4, 2005

(54) WOOD-ENCASED PENCIL FOR WRITING, SKETCHING, DRAWING, AND COSMETIC PURPOSES

(75) Inventors: Udo Beck, Nürnberg (DE); Gerhard Lugert, Nürnberg (DE); Walter Oetter, Stein (DE)

(73) Assignee: Faber-Castell AG, Stein (DE)

( * ) Notice: Subject to any disclaimer, the term of this patent is extended or adjusted under 35 U.S.C. 154(b) by 0 days.

(21) Appl. No.: 10/804,149

(22) Filed: Mar. 17, 2004

(30) Foreign Application Priority Data

Sep. 12, 2003 (DE) ..................... 203 14 274.8

(51) Int. Cl.[7] .................. B43K 19/00; B43K 19/16; B43K 23/008
(52) U.S. Cl. ................. 401/6; 15/443; 16/430
(58) Field of Search ................ 401/6, 7; 15/443; 16/421, 430, DIG. 18, DIG. 19

(56) References Cited

U.S. PATENT DOCUMENTS

| | | | |
|---|---|---|---|
| 4,490,415 A | * 12/1984 | Imamura et al. | 401/88 X |
| 5,735,622 A | * 4/1998 | Melnick et al. | 401/88 X |
| 6,017,594 A | * 1/2000 | Sheets | 401/6 X |
| 6,461,067 B1 | 10/2002 | Beck et al. | 401/7 |

FOREIGN PATENT DOCUMENTS

| EP | 1 177 108 B1 | 2/2002 |
|---|---|---|
| JP | 09039467 A | 2/1997 |

* cited by examiner

*Primary Examiner*—Gene Mancene
*Assistant Examiner*—Kathleen J. Prunner
(74) *Attorney, Agent, or Firm*—Laurence A. Greenberg; Werner H. Stemer; Gregory L. Mayback

(57) ABSTRACT

A wood-encased pencil for writing, sketching, drawing, and cosmetic purposes includes grip surfaces or grip nubs projecting from at least one surface thereof as handling raised structures. The structures are of a plastic material and are applied in the form of an initially flowable preparation which includes at least one plastic and that later solidifies to give the raised structures. In a first variant, the preparation is anhydrous and is of a radiation-curable plastic. In a second variant, the preparation is, likewise, anhydrous, but its solidification is based on physical drying. For such a purpose, the preparation is of an organic solvent as well as a plastic.

37 Claims, 1 Drawing Sheet

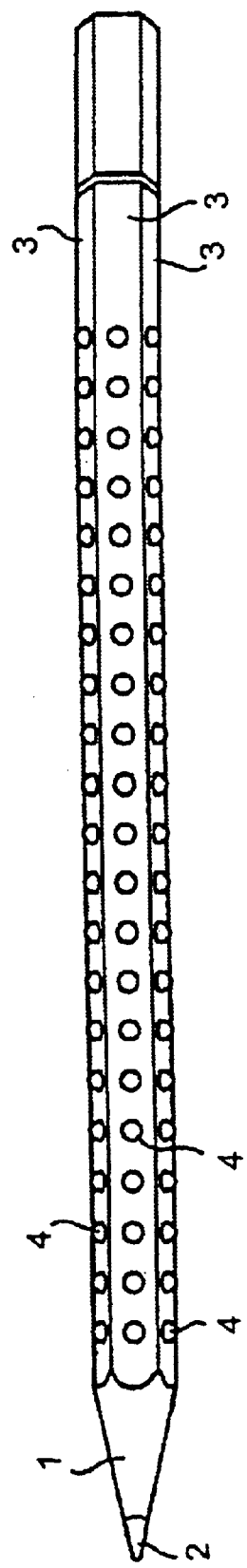

US 6,837,637 B1

WOOD-ENCASED PENCIL FOR WRITING, SKETCHING, DRAWING, AND COSMETIC PURPOSES

CROSS-REFERENCE TO RELATED APPLICATION

This application claims the priority, under 35 U.S.C. § 119, of German patent application No. 203 14 274.8, filed Sep. 12, 2003, which is herewith incorporated by reference in its entirety.

BACKGROUND OF THE INVENTION

Field of the Invention

The invention relates to a pencil for writing, sketching, drawing, and cosmetic purposes, in particular, a wood-encased pencil. Such pencils have a protective jacket accommodating a lead in the center. However, the term pencils should also be understood as meaning pencil-shaped holders for leads. Wood-encased pencils generally have a smooth surface formed by a coat of paint. Holding the pencil is, therefore, associated with a relatively great application of force, which causes fatigue upon extended use.

European Patent EP 1 177 108, corresponding to U.S. Pat. No. 6,461,067 to Beck et al., discloses a pencil of the type mentioned in the introduction in which the surface serving for handling has raised structures made of a plastic material that form grip surfaces or grip nubs. The grippability of the pencil is increased by the presence of the raised structures alone. A further improvement in the grippability and tactile properties can be achieved by selecting an appropriate plastic material. The raised structures in the case of the known pencil are applied to the surface of the pencil in the form of an initially flowable plastic composition, which, then, solidifies or is solidifiable. The main constituent of the plastic composition is an aqueous, water-resistant hardening polymer dispersion or a mixture of such dispersions.

Japanese Patent Document 09/039467 A discloses pencil sleeves made of plastic or metal, to the surfaces of which raised structures are applied in the manner mentioned above. The initially flowable plastic preparation is a mixture of a polyurethane resin, polyol, and at least one hardener for the polyurethane resin. The structures applied to the pencil sleeves in the screen-printing are hardened at temperatures above 80° C. Such temperatures are harmful for painted wooden pencils, which also often contain sensitive leads, meaning that the nubs known from the cited publication cannot be used for wood-encased pencils.

SUMMARY OF THE INVENTION

It is accordingly an object of the invention to provide a wood-encased pencil for writing, sketching, drawing and cosmetic purposes that overcomes the hereinafore-mentioned disadvantages of the heretofore-known devices and methods of this general type and that has raised structures made of an alternative material.

With the foregoing and other objects in view, there is provided, in accordance with the invention, a pencil for writing, sketching, drawing and cosmetic purposes, including a pencil body having at least one surface and raised handling structures of a plastic material disposed on the at least one surface and projecting therefrom to form grip surfaces, the structures being of an initially flowable applied anhydrous preparation of at least one radiation-curable plastic that subsequently solidifies, preferably, under radiation.

With the objects of the invention in view, there is also provided a pencil for writing, sketching, drawing, and cosmetic purposes, including a pencil body having at least one surface and raised handling structures of a plastic material disposed on the at least one surface and projecting therefrom to form grip surfaces, the structures being of an initially flowable applied anhydrous, physically drying preparation including an organic solvent and a plastic that subsequently solidifies.

The structure implied by the process step is patentable over the prior art. This is especially true because the product of the invention of the instant application can only be defined by the process steps, which steps are expected to impart distinctive structural characteristics to the final product.

According to the present invention, the applied preparation is anhydrous and includes a radiation-curable, in particular, a UV-curable, plastic that forms the raised structures after curing. According to another embodiment of the present invention, the preparation is, likewise, anhydrous, but includes, as a main constituent, an organic solvent and a plastic present therein, where this mixture dries physically, i.e., the solvent evaporates and a film or a raised structure is formed from the plastic present in the preparation.

An important advantage of both pencil variants lies in the freedom from water of the preparation, which simplifies the manufacture. In the manufacture of the pencils known from European Patent EP 1 177 108 B1, these pencils have to be stored following application of the aqueous polymer dispersion in drying rooms for up to two days. Accordingly, to be able to accommodate the continuous production of two days, large drying rooms are required, which is associated with high operating costs. The long drying time arises from the slow rate of evaporation of the water from the aqueous plastic dispersions. Such evaporation cannot be significantly shortened by increasing the temperature because the wood casing of the pencils and, often, the lead present therein cannot withstand such an increase. The pencil casing may warp or distort as a result of water being released too rapidly from the wood. As is known, wood casings are produced from two halves glued longitudinally. When using high temperatures, for example, as quoted in Japanese Patent Document 09/039467 A, there is the danger that the glued seam comes apart. In the case of a pencil according to the present invention, by contrast, a separate drying room is no longer required at all. After applying the plastic preparation, the pencils can be conveyed to a UV exposure station where, within, at most, a few seconds, solidification of the raised structures on the wood casing of the pencil takes place. In the case of a solvent-based plastic preparation, the drying time is significantly shortened due to the higher vapor pressure of organic solvents compared with water, meaning that, here, following application of the preparation, drying rooms with a lower capacity are sufficient for drying the pencils.

In accordance with another feature of the invention, the structures are screen-printed structures.

A further problem in the manufacture of pencils of the type under discussion is the handling of the flowable plastic preparation until it is applied to the surface of the pencil. With aqueous plastic dispersions there is the danger that the evaporation of water will result in a thickening of the preparation and, thus, deposition of a plastic film. If such a film is formed in the region of a nozzle or on the screen during application using the screen-printing process, time-consuming cleaning is necessary, which requires the production plant to shut down. A particular disadvantage here is that the polymer films can no longer be dissolved using water. This is different in the case of solvent-based preparations according to another embodiment of the present invention. If deposits form here on tools and equipment, then they can be removed again in a simple manner using the solvent. In the case of preparations according to first embodiment, in which film formation takes place based on UV curing, organic solvents are not required at all or, at worst, are required in a small amount, meaning that the tendency toward the formation of solidified deposits is reduced or is no longer present at all.

Finally, it is also advantageous with both pencil variants that, due to the freedom from water, corrosion of equipment components that come into contact with a preparation is no longer a fear.

In the case of a preparation based on a UV-curable plastic, it is advantageous if the preparation is solvent-free. An increase in the viscosity of the preparation during the manufacturing process as a result of the solvent evaporating is, therefore, excluded. A change in the viscosity of the preparation during the manufacturing process may lead to the shape of the produced raised structures changing as the viscosity of the preparation increases. It is also advantageous that no drying has to be carried out prior to the UV curing in order to remove any solvent still present in the raised structures.

In accordance with a further feature of the invention, the preparation includes a photoinitiator selected from at least one of the group consisting of benzophenone and a benzophenone derivative.

In accordance with an added feature of the invention, the preparation includes a co-initiator enhancing a photoinitiating effect of the photoinitiator.

With the objects of the invention in view, there is also provided a method for making a pencil for writing, sketching, drawing, and cosmetic purposes, including the steps of initially applying a flowable anhydrous preparation of at least one radiation-curable plastic on at least one surface of a pencil body and allowing the preparation to solidify and produce raised handling structures forming grip surfaces projecting from the surface.

With the objects of the invention in view, there is also provided a method for making a pencil for writing, sketching, drawing, and cosmetic purposes, including the steps of initially applying a flowable anhydrous, physically drying preparation including an organic solvent and a plastic on at least one surface of a pencil body and allowing the preparation to physically dry and solidify to produce raised handling structures forming grip surfaces projecting from the surface.

In accordance with an additional feature of the invention, a preferred guide formulation for a preparation envisages that approximately 40 to 98% by weight of UV-curable plastic, approximately 0.1 to 30% by weight of photoinitiator, approximately 0 to 60% by weight of colorant, approximately 0 to 60% by weight of fillers, approximately 0 to 10% by weight of additives, and approximately 0 to 40% by weight of organic solvents are present. Particular preference is given to a preparation with approximately 70 to 80% by weight of acrylate oligomer, approximately 4 to 12% by weight of acrylate monomer, approximately 2 to 8% by weight of benzophenone, approximately 5 to 12% by weight of co-initiator, approximately 1 to 2% by weight of flow-control and slip agent, and approximately 0.5 to 1.5% by weight of antifoam.

In accordance with yet another feature of the invention, a highly suitable UV-curable preparation includes at least one acrylate derivative, which may be a monomer or an oligomer or a mixture thereof. The oligomers used are, advantageously, aromatic and aliphatic epoxy acrylates, polyester-polyurethane, oligoether and amine-modified oligoether acrylates.

In accordance with yet a further feature of the invention, for a physically drying solvent-based preparation, a large number of plastics are suitable, namely, polyesters, phenol resins, urea resins, melamine resins, polyterpene resins, polyvinyl alcohols, polyvinyl acetals, polyvinyl acetates, polyvinyl dispersions, PVC, polyvinyl ethers, polyvinyl propionates, poly(meth)acrylates, poly(meth)acrylate copolymers, polystyrenes, polyolefins, coumarone-indene resins, polyhydantoin, polyamide-imide, naphthalene, formaldehyde and furan resins, hydrocarbon resins, aromatic formaldehyde resins, carbamic acid resins, sulfonamide resins, chloroterphenyl resins, polyamide resins, nitrocelluloses, cellulose acetates, cellulose acetobutyrates, cellulose acetopropionates, ethylcellulose, benzylcellulose, carboxymethyl-, carboxyethyl-, methyl-, hydroxypropylmethyl-, ethylhydroxyethyl- and hydroxyethylcellulose, rubber and rubber derivatives, such as chlorinated rubber, natural rubber, depolymerized natural rubber, cyclized rubber and synthetic rubber, polyurethanes and epoxide resins. Very particularly suitable, however, are preparations that include a PVC copolymer and/or nitrocellulose. A suitable guide formulation for a preparation includes approximately 40 to 90% by weight of organic solvent, approximately 5 to 40% by weight of plastic content, approximately 0 to 40% by weight of colorant, approximately 0 to 50% by weight of fillers, approximately 0 to 20% by weight of waxes, and approximately 0 to 10% by weight of additives. Here and in the formulations given above, additives mean customary auxiliaries such as wetting agents, antifoams, and the like. A particularly suitable preparation includes approximately 40 to 45% by weight of butyl acetate, approximately 10 to 20% by weight of methoxypropyl acetate, approximately 2 to 8% by weight of n-butyl glycolate, approximately 20 to 30% by weight of nitrocellulose, approximately 0.2 to 0.8% by weight of thickener, approximately 0.2 to 0.8% by weight of wax, and approximately 0.4 to 0.12% by weight of antifoam and flow-control agent.

In accordance with a concomitant feature of the invention, both in the case of a pencil according to the first embodiment of the present invention and also in the case of one according to the second embodiment, the preparation may include a filler that is, preferably, chosen from the group consisting of kaolin, talc, barium sulfate, titanium white, calcium carbonate, and mica. By adding such filler, it is possible to vary, within wide ranges, the consistency of the raised structures, which also naturally arises from the type of plastic used. For influencing the tactile properties of the surfaces of the raised structures, fillers can be selected from the group consisting of hollow aluminum silicate beads, expanded hollow beads, soft-feel polyurethane beads, micronized plastics, such as polypropylene or PTFE, and PE waxes.

Preferably, the pencil body is wood-encased.

Other features that are considered as characteristic for the invention are set forth in the appended claims.

Although the invention is illustrated and described herein as embodied in a wood-encased pencil for writing, sketching, drawing and cosmetic purposes, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWING

The FIGURE is a plan view of a pencil with a wooden casing and a pencil lead according to the invention.

DESCRIPTION OF THE PREFERRED EMBODIMENTS

Referring now to the single FIGURE of the drawing, it is seen that a pencil has a wooden casing 1 and a pencil lead 2. The pencil has a hexagonal contour. Nubs 4 project from the individual hexagonal surfaces 3 in a substantially radial direction. Instead of nubs, other structures may be applied to the surface of the pencil, for example, strip-like, punctiform, or any other structures that extend in the longitudinal direction of the pencil. It is also conceivable for the raised structure to extend around the pencil periphery in a ring shape. The raised structures or nubs may be applied either to a blank or uncolored wood surface, or to one provided with a coat of paint.

Some examples of formulations of plastic preparations are given in the text below. The percentages relate to the plastic composition in the flowable, i.e., as yet unhardened, starting state. All percentages are percent by weight unless stated otherwise.

EXAMPLE 1

A UV crosslinkable system for transparent or colorless surface structures for wood-encased pencils.

| | |
|---|---|
| Acrylate oligomer (Ebecryl 600/35 OT) | 76.5% |
| Acrylate monomer (Ebecryl 40) | 8% |
| Benzophenone (photoinitiator) | 4% |
| Reactive tertiary amine (co-initiator) | 8% |
| Hydroxycyclohexyl phenyl ketone (co-initiator) | 1% |
| Flow-control and slip agent | 1.5% |
| Antifoam | 1% |

The UV curable acrylates Ebecryl 600/35 OT and Ebecryl 40 are available from UCB Chemie GmbH, Kerpen, Germany 50170. The tertiary amine used is manufactured, for example, by CIBA Spezialitatenchemie, Lampertheim, Germany 68632. After structures have been applied to wood-encased pencils, crosslinking is achieved by irradiating with UV light. The flow-control and slip agent used is TEGO Glide 440, and the antifoam used is TEGO Airex 900, both products from TEGO Chemie Service GmbH, Essen, Germany 45139.

The application of the preparation to a wood-encased pencil is carried out by screen-printing. Shortly after application of the preparation, the pencil is passed to a UV irradiation station, where, after UV irradiation, virtually immediate curing starts. Besides UV, an irradiation with electrons is also suitable. A photoinitiator is not necessary here.

EXAMPLE 2

A UV-crosslinkable system, solvent-free, for black colored surface structures.

| | |
|---|---|
| Polyester acrylate (Laromer LR 9004, BASF) | 93.6% |
| Pigment preparation (Black 550920/N50, Coates Screen Inks) | 3.4% |
| Alpha-hydroxy ketone photoinitiator (Darocure 1173, Ciba) | 2.0% |
| Acylphosphine oxide photoinitiator (Lucirin TPO, BASF) | 1.0% |

The application to a pencil casing and curing takes place as in example 1.

EXAMPLE 3

A Solvent-based system.

| | |
|---|---|
| Butyl acetate (solvent) | 45% |
| Methoxypropyl acetate (solvent) | 15% |
| n-Butyl glycolate (solvent) | 5% |
| Nitrocellulose (plastic) | 24% |
| Calcium carbonate (filler) | 9% |
| Thickener, Aerosil 200, Degussa | 0.5% |
| Wax additive | 0.5% |
| Antifoam | 0.8% |
| Flow-control agent | 0.2% |

Nitrocellulose is available, for example, in the form of chips from Hagedorn AG, Lingen, Germany 49808, under the name H-24, and the wax is available from Lawter International Belgium, N.V. under the name Polysperse E. The antifoam used is the product "No air liquid" prepared by Bärlocher, and the flow-control agent used is Dow Corning 57. The latter is a product of Dow Jones, Wiesbaden, Germany 65201. The preparation is, likewise, applied in a screen-printing process. The pencils are, then, dried to remove the solvent from the raised structures.

We claim:

1. A pencil for writing, sketching, drawing and cosmetic purposes, comprising:

a pencil body having at least one surface; and raised handling structures of a plastic material disposed on said at least one surface and projecting therefrom to form grip surfaces, said structures being of an initially flowable applied anhydrous preparation of at least one radiation-curable plastic that subsequently solidifies.

2. The pencil according to claim 1, wherein said preparation is solvent-free.

3. The pencil according to claim 1, wherein said preparation includes a UV-curable plastic.

4. The pencil according to claim 3, wherein said preparation includes a photoinitiator selected from at least one of the group consisting of benzophenone and a benzophenone derivative.

5. The pencil according to claim 4, wherein said preparation includes a co-initiator enhancing a photoinitiating effect of said photoinitiator.

6. The pencil according to claim 5, wherein said preparation has a guide formulation by percentage weight of:

| | |
|---|---|
| UV-curable plastic | 40–98%; |
| Organic solvent | 0–40%; |
| Photoinitiator | 0.1–30%; |
| Colorant | 0–60%; |

-continued

| Fillers | 0–60%; and |
|---|---|
| Additives | 0–10%. |

7. The pencil according to claim 6, wherein:
said preparation includes at least one acrylate derivative selected from the group consisting of an acrylate monomer and an acrylate oligomer; and
said acrylate oligomer selected from the group consisting of aromatic and aliphatic epoxide resins, polyester-, polyurethane-, oligoether-, amine-modified oligoethers and polyol acrylates.

8. The pencil according to claim 7, wherein said preparation has a guide formulation by percentage weight of:

| Acrylate oligomer | 70–80%; |
|---|---|
| Acrylate monomer | 4–12%; |
| Benzophenone | 2–8%; |
| Co-initiator | 5–12%; |
| Flow-control and slip agent | 1–2%; and |
| Antifoam | 0.5–1.5%. |

9. The pencil according to claim 6, wherein said preparation includes at least one filler selected from the group consisting of kaolin, talc, barium sulfate, titanium white, calcium carbonate, and mica.

10. The pencil according to claim 6, wherein said preparation includes at least one filler selected from the group consisting of hollow aluminum silicate beads, expanded hollow beads, soft-feel PU beads, micronized plastics, such as polypropylene or PTFE, and PE waxes.

11. The pencil according to claim 1, wherein said preparation has a guide formulation by percentage weight of:

| UV-curable plastic | 40–98%; |
|---|---|
| Organic solvent | 0–40%; |
| Photoinitiator | 0.1–30%; |
| Colorant | 0–60%; |
| Fillers | 0–60%; and |
| Additives | 0–10%. |

12. The pencil according to claim 11, wherein:
said preparation includes at least one acrylate derivative selected from the group consisting of an acrylate monomer and an acrylate oligomer; and
said acrylate oligomer selected from the group consisting of aromatic and aliphatic epoxide resins, polyester-, polyurethane-, oligoether-, amine-modified oligoethers and polyol acrylates.

13. The pencil according to claim 12, wherein said preparation has a guide formulation by percentage weight of:

| Acrylate oligomer | 70–80%; |
|---|---|
| Acrylate monomer | 4–12%; |
| Benzophenone | 2–8%; |
| Co-initiator | 5–12%; |
| Flow-control and slip agent | 1–2%; and |
| Antifoam | 0.5–1.5%. |

14. The pencil according to claim 11, wherein said preparation includes at least one filler selected from the group consisting of kaolin, talc, barium sulfate, titanium white, calcium carbonate, and mica.

15. The pencil according to claim 11, wherein said preparation includes at least one filler selected from the group consisting of hollow aluminum silicate beads, expanded hollow beads, soft-feel PU beads, micronized plastics, such as polypropylene or PTFE, and PE waxes.

16. The pencil according to claim 1, wherein said preparation includes at least one filler selected from the group consisting of kaolin, talc, barium sulfate, titanium white, calcium carbonate, and mica.

17. The pencil according to claim 1, wherein said preparation includes at least one filler selected from the group consisting of hollow aluminum silicate beads, expanded hollow beads, soft-feel PU beads, micronized plastics, such as polypropylene or PTFE, and PE waxes.

18. The pencil according to claim 1, wherein said structures are screen-printed structures.

19. The pencil according to claim 1, wherein said structures are of an initially flowable applied anhydrous preparation of at least one radiation-curable plastic subsequently solidifying under radiation.

20. The pencil according to claim 1, wherein said pencil body is of wood.

21. A method for making a pencil for writing, sketching, drawing, and cosmetic purposes, which comprises:
initially applying a flowable anhydrous preparation of at least one radiation-curable plastic on at least one surface of a pencil body; and
allowing the preparation to solidify and produce raised handling structures forming grip surfaces projecting from the surface.

22. The method according to claim 21, which further comprises carrying out the applying step by screen-printing the preparation.

23. A pencil for writing, sketching, drawing, and cosmetic purposes, comprising:
a pencil body having at least one surface; and
raised handling structures of a plastic material disposed on said at least one surface and projecting therefrom to form grip surfaces, said structures being of an initially flowable applied anhydrous, physically drying preparation including an organic solvent and a plastic that subsequently solidifies.

24. The pencil according to claim 23, wherein said preparation includes at least one plastic selected from the group consisting of polyesters, phenol resins, urea resins, melamine resins, polyterpene resins, polyvinyl alcohols, polyvinyl acetals, polyvinyl acetates, polyvinyl dispersions, PVC, polyvinyl ethers, polyvinyl propionates, poly(meth) acrylates, poly(meth)acrylate copolymers, polystyrenes, polyolefins, coumarone-indene resins, polyhydantoin, polyamide-imide, naphthalene, formaldehyde and furan resins, hydrocarbon resins, aromatic formaldehyde resins, carbamic acid resins, sulfonamide resins, chloroterphenyl resins, polyamide resins, nitrocelluloses, cellulose acetates, cellulose acetobutyrates, cellulose acetopropionates, ethylcellulose, benzylcellulose, carboxymethyl-, carboxyethyl-, methyl-, hydroxypropylmethyl-, ethylhydroxyethyl- and hydroxyethylcellulose, rubber and rubber derivatives, such as chlorinated rubber, natural rubber, depolymerized natural rubber, cyclized rubber and synthetic rubber, polyurethanes, and epoxide resins.

25. The pencil according to claim 23, wherein said preparation includes one material selected from the group consisting of a PVC copolymer and nitrocellulose.

26. The pencil according to claim 23, wherein said preparation has a guide formulation by percentage weight of:

| | |
|---|---|
| Organic solvent | 40–90%; |
| Plastic content | 5–40%; |
| Colorant | 0–40%; |
| Fillers | 0–50%; |
| Waxes | 0–20%; and |
| Additives | 0–10%. |

27. The pencil according to claim 26, wherein said preparation has a guide formulation by percentage weight of:

| | |
|---|---|
| Butyl acetate | 40–45%; |
| Methoxypropyl acetate | 10–20%; |
| n-Butyl glycolate | 2–8%; |
| Nitrocellulose | 20–30%; |
| Filler | 5–15%; |
| Thickener | 0.2–0.8%; |
| Wax | 0.2–0.8%; |
| Antifoam | 0.4–0.12%; and |
| Flow-control agent | 0.1–0.3%. |

28. The pencil according to claim 27, wherein said preparation includes at least one filler selected from the group consisting of kaolin, talc, barium sulfate, titanium white, calcium carbonate, and mica.

29. The pencil according to claim 27, wherein said preparation includes at least one filler selected from the group consisting of hollow aluminum silicate beads, expanded hollow beads, soft-feel PU beads, micronized plastics, such as polypropylene or PTFE, and PE waxes.

30. The pencil according to claim 26, wherein said preparation includes at least one filler selected from the group consisting of kaolin, talc, barium sulfate, titanium white, calcium carbonate, and mica.

31. The pencil according to claim 26, wherein said preparation includes at least one filler selected from the group consisting of hollow aluminum silicate beads, expanded hollow beads, soft-feel PU beads, micronized plastics, such as polypropylene or PTFE, and PE waxes.

32. The pencil according to claim 23, wherein said preparation includes at least one filler selected from the group consisting of kaolin, talc, barium sulfate, titanium white, calcium carbonate, and mica.

33. The pencil according to claim 23, wherein said preparation includes at least one filler selected from the group consisting of hollow aluminum silicate beads, expanded hollow beads, soft-feel PU beads, micronized plastics, such as polypropylene or PTFE, and PE waxes.

34. The pencil according to claim 23, wherein said structures are screen-printed structures.

35. The pencil according to claim 23, wherein said pencil body is of wood.

36. A method for making a pencil for writing, sketching, drawing, and cosmetic purposes, which comprises:
initially applying a flowable anhydrous, physically drying preparation including an organic solvent and a plastic on at least one surface of a pencil body; and
allowing the preparation to physically dry and solidify to produce raised handling structures forming grip surfaces projecting from the surface.

37. The method according to claim 36, which further comprises carrying out the applying step by screen-printing the preparation.

* * * * *